(12) United States Patent
Risk (10) Patent No.: US 7,520,186 B2
(45) Date of Patent: Apr. 21, 2009

(54) APPARATUS AND METHOD FOR MEASURING SOIL GASES

(75) Inventor: David A. Risk, Heatherton (CA)

(73) Assignee: St. Francis Xavier University, Antigonish, Nova Scotia (CA)

( * ) Notice: Subject to any disclaimer, the term of this patent is extended or adjusted under 35 U.S.C. 154(b) by 232 days.

(21) Appl. No.: 11/419,082

(22) Filed: May 18, 2006

(65) Prior Publication Data

US 2007/0266800 A1    Nov. 22, 2007

(30) Foreign Application Priority Data

May 18, 2005   (CA)   .................................... 2507354

(51) Int. Cl.
*G01N 1/10* (2006.01)

(52) U.S. Cl. ................. 73/864.74; 73/863.23

(58) Field of Classification Search ............. 73/863.23, 73/864.74, 864.81, 864.51
See application file for complete search history.

(56) References Cited

U.S. PATENT DOCUMENTS

| | | | | |
|---|---|---|---|---|
| 2,210,546 | A | * | 8/1940 | Hassier .................... 73/864.74 |
| 3,685,345 | A | * | 8/1972 | Wise ........................... 73/19.1 |
| 4,759,227 | A | * | 7/1988 | Timmons ................. 73/863.23 |
| 5,010,776 | A | * | 4/1991 | Lucero et al. ............. 73/863.23 |
| 5,355,739 | A | * | 10/1994 | Cooper et al. ............. 73/864.73 |
| 5,639,956 | A | * | 6/1997 | Christy ...................... 73/19.01 |
| 6,289,714 | B1 | * | 9/2001 | Tartre ........................ 73/19.01 |
| 2004/0154414 | A1 | * | 8/2004 | LaCourse et al. ......... 73/863.23 |

FOREIGN PATENT DOCUMENTS

| | | |
|---|---|---|
| CA | 1112551 | 11/1981 |
| CA | 1227066 | 9/1987 |
| CA | 1311886 | 12/1992 |
| CA | 2072467 | 12/1993 |
| CA | 1327259 | 3/1994 |
| CA | 2193000 | 2/1996 |
| CA | 2215321 | 9/1996 |
| CA | 2220968 | 12/1996 |
| CA | 2272277 | 4/1997 |
| CA | 2307782 | 10/1998 |

OTHER PUBLICATIONS

Vaisala, User's Guide, Vaisala CARBOCAP Carbon Dioxide Probe GMP 343, Apr. 2005, 70 pages.
Risk et al., A new technique for in-situ soil gas diffusivity measurement, presented at AGU Spring Meeting, May 21, 2004.

* cited by examiner

*Primary Examiner*—Robert R Raevis
(74) *Attorney, Agent, or Firm*—Bereskin & Parr

(57) ABSTRACT

A probe for sampling a soil gas comprising a body having a cavity to which is connected an inlet and an outlet, and a gas permeable waterproof membrane wrapped around the body and sealing the cavity. The membrane allows the soil gas to flow across the membrane from the soil to the cavity. A method for measuring soil gas diffusivity comprising the step of circulating in a closed loop a carrier gas substantially at an atmospheric pressure through a diffusion gas sampling probe inserted in the soil and through a sensor used for the measurement of a concentration of at least a component of the soil gas.

22 Claims, 6 Drawing Sheets

FIG_4

FIG_5

FIG_6

FIG_7

APPARATUS AND METHOD FOR MEASURING SOIL GASES

FIELD OF THE INVENTION

The present invention relates generally to soil gas measurement. More specifically, the invention relates to a new probe, system and method for measuring concentrations and diffusivity of soil gases.

BACKGROUND OF THE INVENTION

In temperate forests, soil respiration accounts for approximately half of total forest respiration and is regarded as the least well understood component of landscape carbon balance. Many research efforts have been aimed at determining the physical controls on total soil respiration and to that end, a wide variety of methods have been employed. The large-scale eddy covariance towers that are in operation at many key research sites are not able to resolve $CO_2$ dynamics at the soil level and therefore surface based $CO_2$ measurements are required. Subsurface approaches to soil $CO_2$ monitoring are becoming increasingly popular. While requiring substantially more equipment than surface flux measurements, and limited in terms of spatial coverage and averaging, they offer significant advantages for resolving soil gas processes. Advantages include excellent vertical resolution of $CO_2$ dynamics in the layered soil system, and the ability to estimate instantaneous $CO_2$ production at specific depths. Such soil $CO_2$ production estimates are helping to clarify temperature controls on soil respiration processes. This is especially true for shorter time scales when measured surface fluxes may often lag well behind actual $CO_2$ production due to $CO_2$ storage in the soil profile.

When used in conjunction with a diffusion model to determine instantaneous $CO_2$ production, subsurface methods require good estimates of effective soil gas diffusivity (De). Concentration profiles of natural, injected $^{222}$Radon, or other tracers, have been used to determine diffusivity in the field. However, many researchers defer to empirically-derived approximations such as the Millington model or improved models requiring soil-specific input parameters. Unfortunately, diffusivity models tend to perform less well in some soils than in others.

There are several approaches that allow for laboratory testing of intact soil cores collected in the field. These have the advantage that soil gas diffusivity can be determined on a relatively fine scale that would be difficult to measure with $^{222}$Radon concentration profiles, and in highly organic substrates such as soil litter that are not clearly dealt with in diffusivity model approximations. There remains, however, the potential for changes to soil physical properties (e.g. soil aggregation, compaction etc) that could have a large influence on resulting values. Consequently, it would be desirable to directly evaluate soil gas diffusivity in the field, as this would minimize potential problems with alteration to diffusivity in extracted soil cores and allows for field conditions to be monitored in-situ at the time of soil gas measurement.

Soil pore spaces are filled with varying quantities of air and water, and typical soil gas/vapour/liquid sampling techniques involve a buried probe that permits air, when present, to be withdrawn from the soil profile and contained for later analysis. Canadian patents CA 2215321 to Heller et al and CA 2072467 to Vollweiler illustrate such techniques. However, these methods can not make measurements without disturbing the soil air profile.

There is therefore a need for an apparatus and a method that allow continuous in-situ soil gas concentration and diffusivity measurements and that do not disturb the soil air profile.

SUMMARY OF THE INVENTION

In accordance with a first aspect of the present invention, there is provided a probe for sampling soil gas in situ comprising a body having a cavity and a waterproof membrane covering said cavity, and having an inlet communicating with the cavity for introducing a carrier gas, and an outlet communicating with the cavity for exhausting the carrier gas to a gas sensor, the waterproof membrane being permeable to the soil gas such that when the probe is positioned in a soil gas measurement site, soil gas diffuses into the cavity and can combine with an introduced carrier gas and be exhausted therewith to the gas sensor.

Preferably, the body is elongate and said inlet and outlet are located a first end thereof. The cavity may be designed such that it has a longitudinal wall substantially separating the cavity into two chambers. The wall has an aperture remote from said inlet and said outlet for allowing fluid communication between the two chambers. Optionally, the probe further comprises a gas sensor for measuring a concentration of a component of said soil gas. Preferably, the probe is equipped with a mesh around the membrane to protect it from being substantially deformed by the soil. When the probe is not equipped with its own gas sensor, a first tube is connected at one end to the inlet and at the other end to a carrier gas supply. A second tube is similarly connected at one end to the outlet and at the other end to test equipment having a gas sensor for measuring the concentration of a component of the soil gas.

Optionally, the probe may comprise a pointed tip at a first end for facilitating its insertion in the soil. This may be accomplished simply by pushing on the probe or by hammering on it. In this case, the inlet and the outlet are located at a second end of the body remote from the first end such that they do not get damaged during insertion on the soil. Preferably, the probe has a peripheral enlargement of its body which is longitudinally located between the second end and the membrane. Optionally, the probe is equipped with a shaft that is connected at the second end for inserting the probe in soil such that the probe does not get damaged by hammering. The shaft further provides a grip to insert the probe by hand.

Preferably, the probe has a cylindrical body which may be made of plastic or metal.

In accordance with a second aspect of the present invention, there is provided a soil gas measurement system comprising a probe as previously defined, a supply of a carrier gas, a gas sensor for measuring the concentration of at least one component of the soil gas in the carrier gas, a datalogger for logging data, a pump for circulating the carrier gas and a controller for controlling the gas sensor and the datalogger. The gas sensor and the pump are fluidly connected to the probe through the inlet and the outlet, the pump circulating the carrier gas in a closed-loop circuit from the probe to the sensor and back to the probe, and the gas sensor operatively communicating with the datalogger. Preferably, the measurement system further comprises means to eliminate the at least one component of the soil gas from the probe prior to the measuring step by the gas sensor. More preferably, the closed-loop circuit has low internal pressure gradients so as to not interfere with the diffusivity of the soil gas.

In accordance with a third aspect of the present invention, there is provided a method for taking measurements of a soil gas in situ comprising the step of circulating in a closed loop a carrier gas substantially at an atmospheric pressure through a diffusion soil gas sampling probe positioned below the surface of a soil site, and through a gas sensor for the measurement of a concentration of at least one component of the soil gas. Preferably, diffusive equilibration of the soil gas in said carrier gas is allowed to take place. Optionally, an equilibrated concentration may be determined using a mathematical model. Advantageously, the carrier gas is substantially free of at least one component contained in the soil gas prior to allowing diffusion of the soil gas so that the concentration of the component in question is known to be close to zero. Optionally, the probe is positioned below the surface of the soil site by being driven into the soil site by applying a downward force on its shaft, if such a model of probe is used.

There are several benefits to the invention in comparison to existing methods for measuring soil gas concentrations. Firstly, samples of soil gas do not need to be removed from the soil profile to measure concentration, because measurements are made through the probe by diffusive equilibration. This minimal level of disturbance is often required for research applications, and also facilitates repeated and continuous soil gas concentration measurements over long periods of time if necessary, without altering the soil environment.

Secondly, the invention provides a practical, fast and field portable method for measuring the potential diffusive transport rate of gases through the soil matrix. Gas diffusion is an important variable in many processes, including soil emissions of greenhouse gases (such as carbon dioxide, nitrous oxide, methane), radon transport towards building foundations, and decomposition of hydrocarbon soil contaminants. Soil diffusion rates are highly site specific and very difficult to predict, but the invention provides direct measurements of the diffusion coefficient, which is a necessary variable in many types of environmental inquiry.

BRIEF DESCRIPTION OF DRAWINGS

These and other features of the present invention will become more apparent from the following description in which reference is made to the appended drawings wherein.

DETAILED DESCRIPTION OF THE INVENTION

Figure 1:
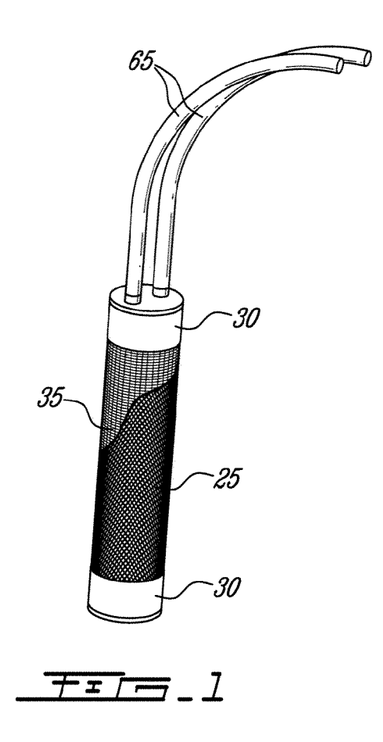
FIG. 1 shows a perspective view of a probe in accordance with an embodiment of the present invention.
Figure 2:
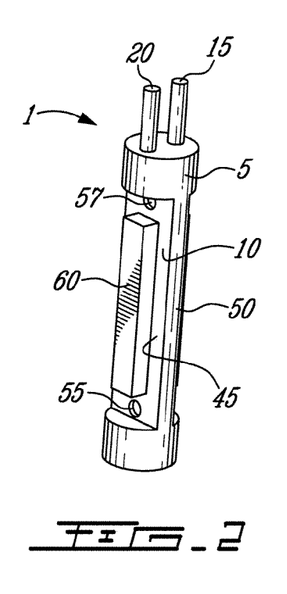
FIG. 2 shows a perspective view of the probe of FIG. 1 with its mesh and membrane removed to illustrate the probe body interior.
Figure 3:
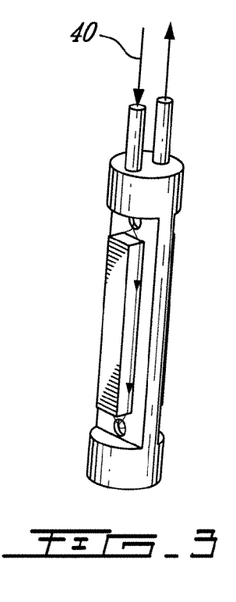
FIG. 3 shows a perspective view of the probe of FIG. 2 depicting the flow of the carrier gas.

FIGS. 1 to 3 show a probe 1 intended to be buried more or less permanently in a soil gas measurement site. The probe comprises a body 5 having a cavity 10. Connected to the cavity 10 are an inlet 15 and an outlet 20. FIG. 2 shows a waterproof, microporous gas permeable membrane 25 wrapped around the body 5 and sealed with sealing means such as a sealing tape 30, for example. The membrane 25 seals the cavity 10 such that in use, soil gases 27 have to diffuse through the membrane 25 into the cavity 10. The membrane 25 may be bonded to the body 5. The cavity 10 contains a volume of air protected by the membrane 25 whose specific characteristics are selected to suit the application, in particular the required water column waterproofness, while maximizing diffusive potential.

The body 5 itself may be manufactured from metal or plastic. The membrane is covered with a tight-fitting fine stainless steel mesh 35 (partially shown) to help retain the shape of the membrane 25 against the pressure of surrounding soil particles. As shown in FIG. 3, a carrier gas 40 is circulated in the cavity 10 through the inlet 15 and back through the outlet 20. The carrier gas 40 circulates in passages 45 of the cavity 10. These passages 45 are sized proportionally to the carrier gas rate. Because the probe 1 relies on diffusion, it is important that pressures in the system are kept at atmospheric pressure. Bernoulli pressure gradients are easily modeled for different flow rates and flow channel geometries. Bernoulli pressure gradients can develop with fast flow rates, so flow speed is kept low with wide passages 45. The carrier gas 40 arrives by the inlet 15, moves underneath the membrane 25 in the passages 45 through the cavity 10, flows to the other side of the wall 50, separating the cavity 10 in two, through aperture 55 and back to the outlet 20. This provides maximal exposure to the membrane surface. Wall 50 and blocks 60 provide support for the membrane 25 and mesh 35 to prevent compression by soil particles. Depressions 57 are present on each side of the wall to allow a closer placement of inlet 15 and outlet 20, permitting a more compact design of the probe. The cavity 10 may adopt many designs, but the basic concept is to promote circulation of the carrier gas 40 close to the membrane 25 such that soil gases 27 may diffuse in the carrier gas 40.

Figure 4:
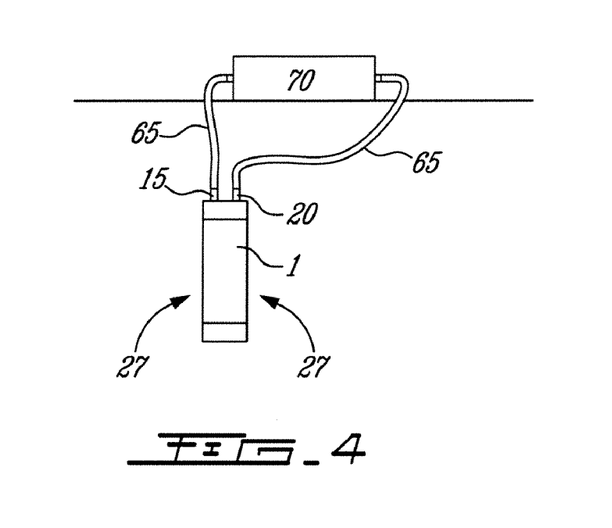
FIG. 4 shows a partially cut-away side view of the measurement system in accordance with another embodiment of the invention.
Figure 5:
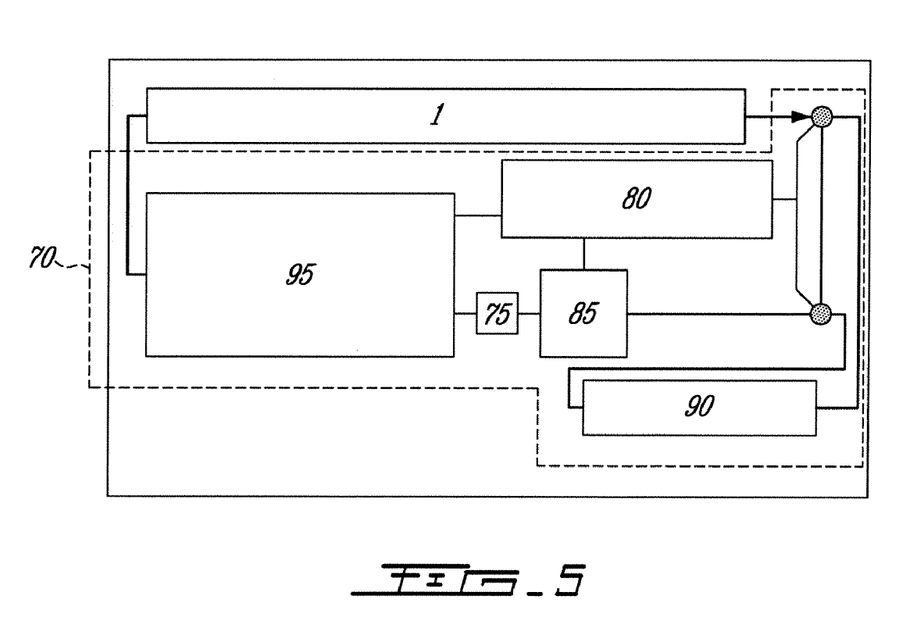
FIG. 5 shows a schematic view of the measurement system in accordance with another embodiment of the invention.

As shown in FIGS. 3 and 4, the probe 1 is provided with tubes 65 between both the inlet 15 and the outlet 20 and test equipment 70. FIG. 5 shows a schematic of the connections between the probe 1 and the test equipment 70. It may be seen that the carrier gas 40 is circulated in a closed loop between the probe 1 and the test equipment 70. The test equipment 70 comprises a gas sensor 75 placed in the carrier gas 40, a datalogger 80 for recording measurements taken by the gas sensor 75, a pump 85 for providing motion to the carrier gas 40. It may be possible to use more than one gas sensor 75, each gas sensor having a different concentration range and associated different resolutions. Hence, depending on the concentration of soil gas 27 in the carrier gas 40, a particular gas sensor 75 may be selected to optimize the resolution. Optionally, the carrier gas 40 may initially be freed from a component to be measured (such as $CO_2$, for example) in the soil gas 27 by using filtering means 90. Such filtering means may be soda lime columns or a purging gas which is free of the component of be measured. A controller 95 controls the interactions of components of the test equipment 70.

In an alternative embodiment, the gas sensor 75 may be placed directly in the probe 1, in contact with the gas contained in the cavity 10. However, where the probe 1, gas sensor 75, and associated hardware are not integral to one another, they can preferably be de-coupled and re-coupled so that the gas sensor 75 and associated hardware can be used with many different buried probes 1.

Figure 6:
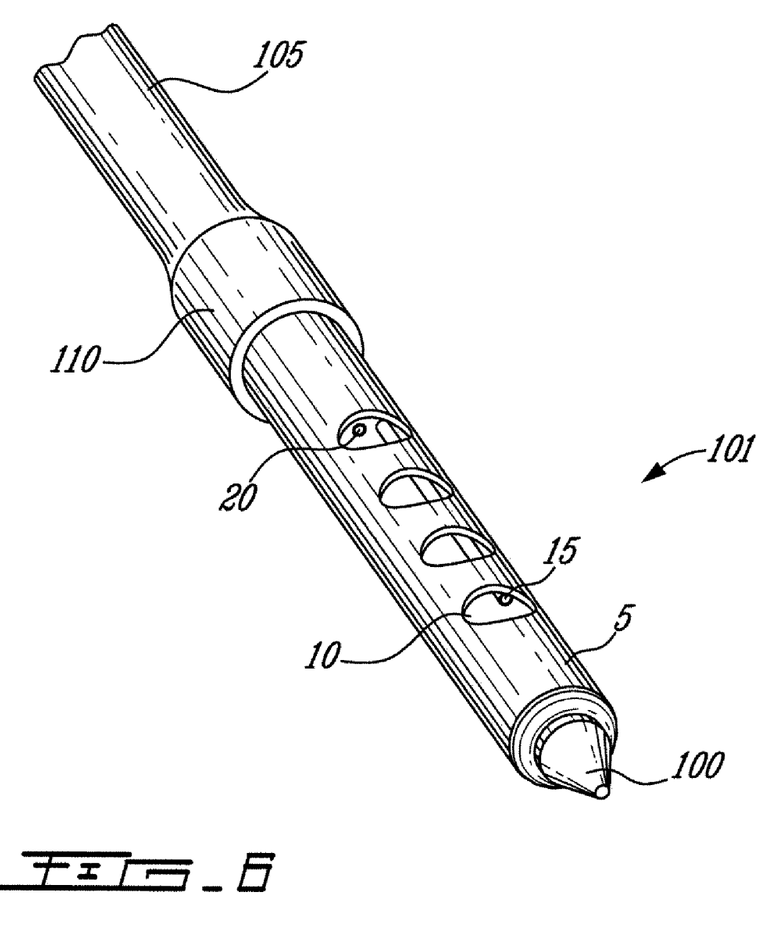
FIG. 6 shows a perspective view of a probe in accordance with another embodiment of the invention.
Figure 7:
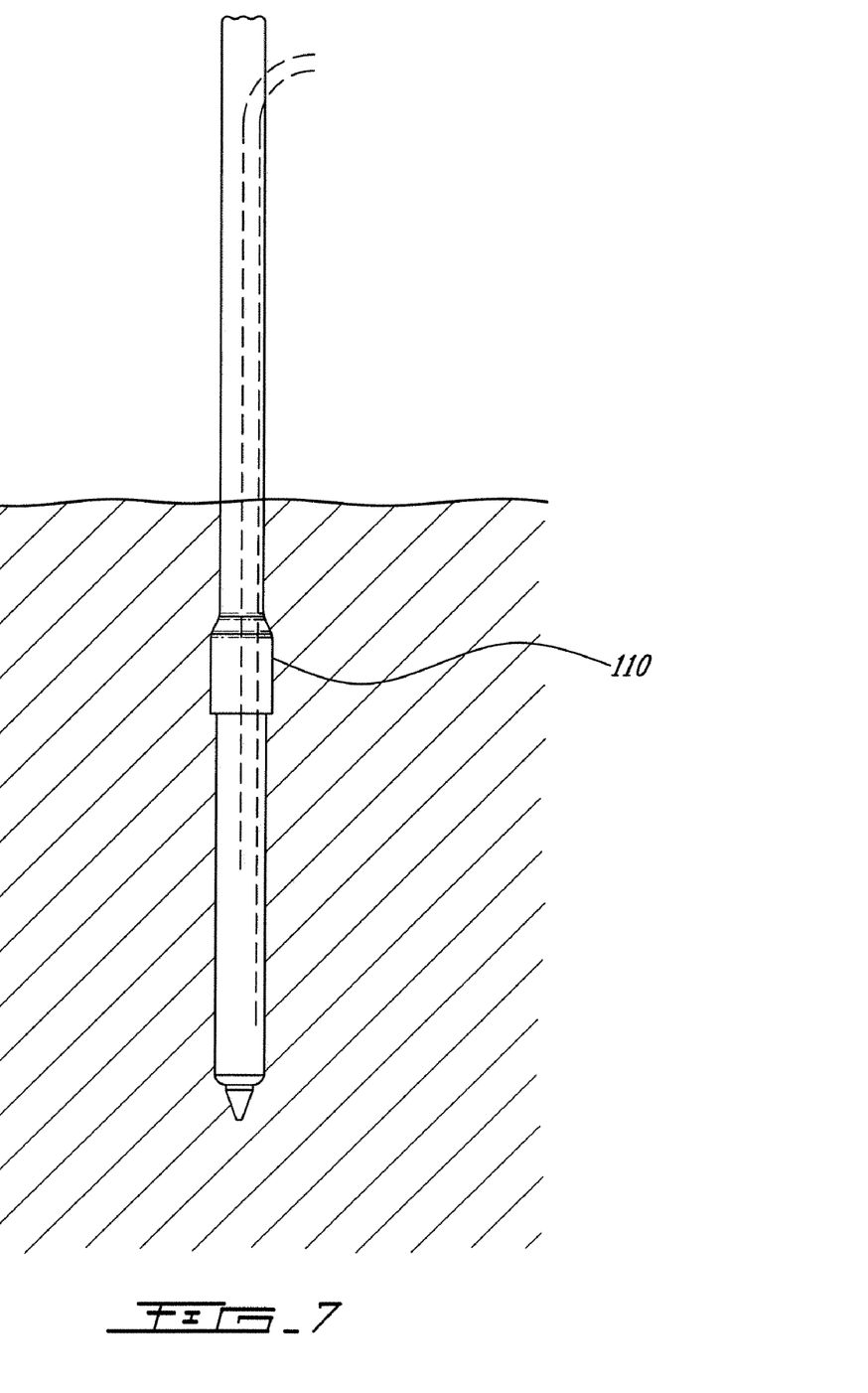
FIG. 7 shows a partially cut-away side view of the probe of FIG. 6 installed in the ground.

FIG. 6 depicts another embodiment of a probe having a drive-point. This type of probe 101 may be driven directly in the ground by hand or with a hammer, rather than being buried as described previously. The drive-point probe otherwise works in a similar manner as the model previously described. However, it has a pointed tip 100 for easier insertion into the ground, a shaft 105 for grabbing the probe 101 and an enlarged section 110 for sealing the hole in which the probe is inserted. The shaft 105 is preferably capable of withstanding hammering, which may be necessary to insert the probe 101 in the ground. The shaft 105 is also used to remove the probe 101 from the ground. FIG. 7 shows a view of the probe 101 inserted in the soil, highlighting the enlarged section 110 that prevents soil gases 27 from escaping around the probe 101. In contrast, the permanent burial probes previously described can only be removed by digging. Both permanent and drive-point probes can be installed via the surface (vertical installation) or a pit (horizontal installation). When deployed in the field, the permanent burial probes are allowed to settle for 1-2 weeks before making measurements, while the drive-point probes can be used immediately as a result of superior hole sealing characteristics.

Figure 8:
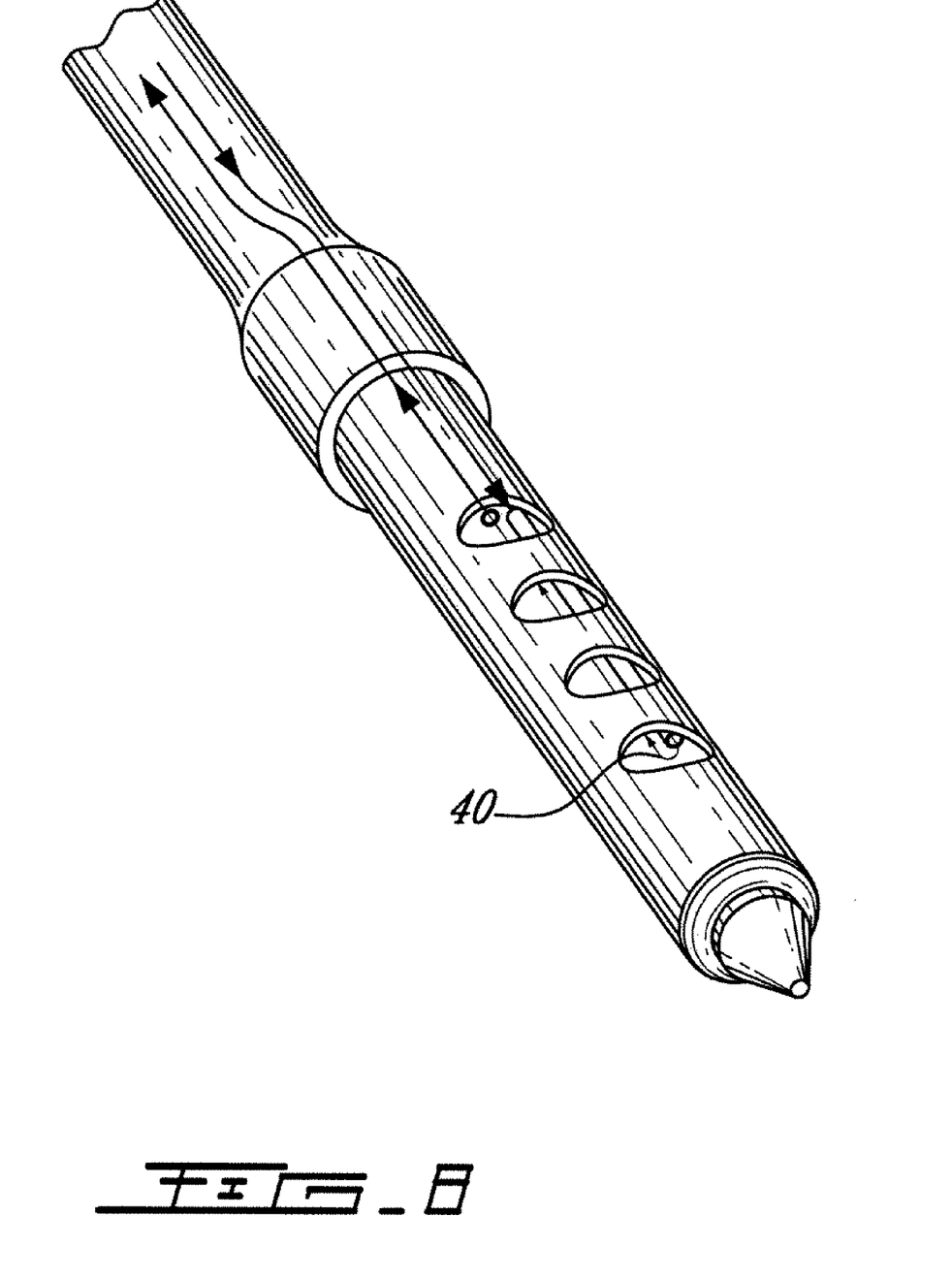
FIG. 8 shows a perspective view of the probe of FIG. 6, highlighting the carrier gas.
Figure 9:
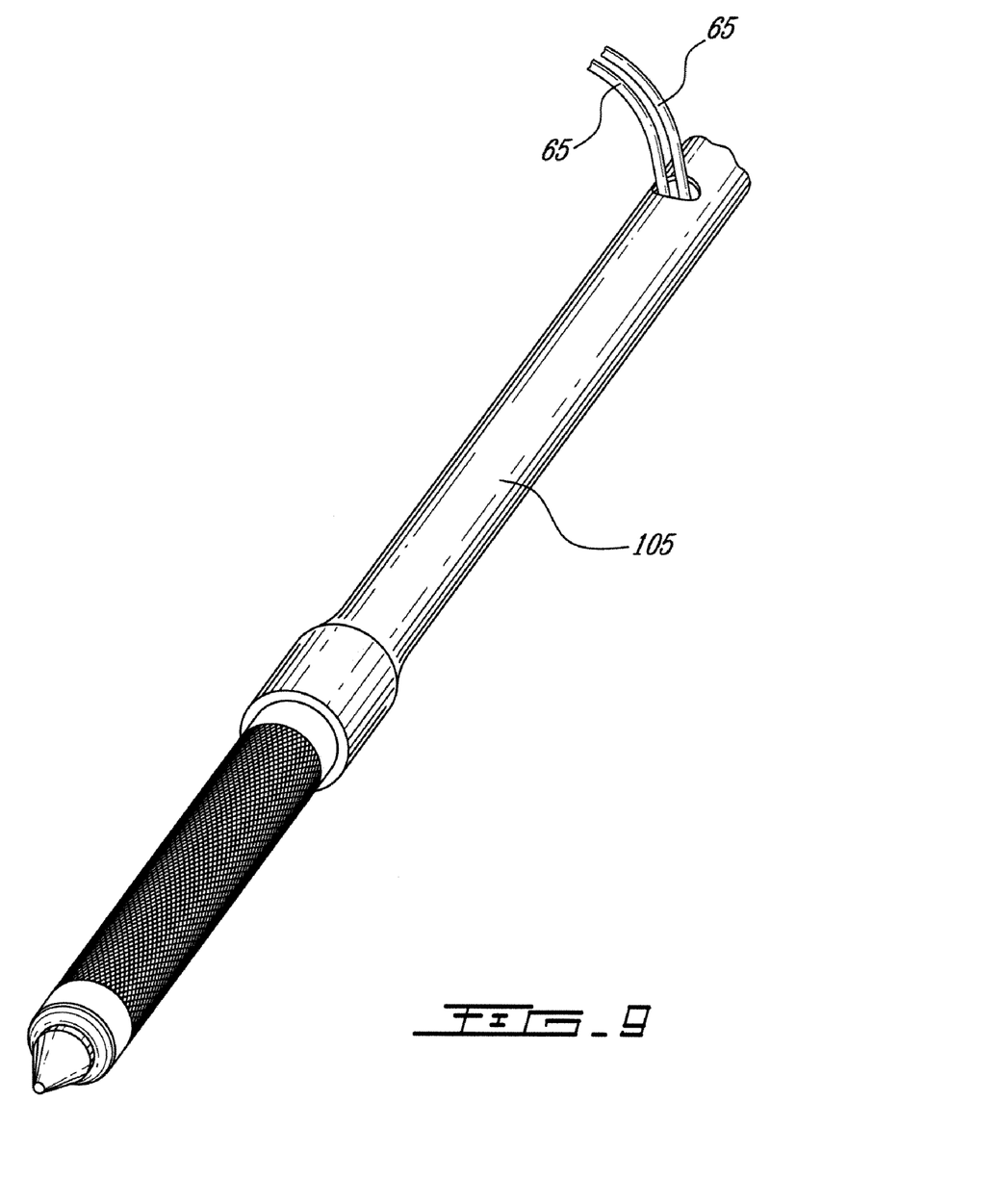
FIG. 9 shows a perspective view of the probe of FIG. 6 with the membrane in place.

FIG. 8 shows the flow of the carrier gas 40. It may be noted that the cavity 10 adopts a different configuration in this probe. In fact, the person skilled in the art will appreciate that many different shapes and configuration could be used for the probe bodies and their cavities. The important aspects are to keep pressure gradients as low as possible in the closed-loop and to try to maximize contact of the carrier gas 40 with the membrane 25.

In use, the probe 101 is buried or driven into the soil. Its inlet 15 and outlet 20 are connected to the test equipment 70 such that a closed loop is formed in which will circulate the carrier gas 40. Optionally, the carrier gas 40 may be initially purged from a particular component of the soil gas 27 which is intended to be measured, or filtered through filtering means 90. The pump 85 circulates the carrier gas 40. As diffusion occurs through the membrane 25, soil gas components flow with the carrier gas 40 to the gas sensor 75. The gas sensor 75 measures the concentration of the component in the carrier gas 40 and sends the measurement to the datalogger 80. The carrier gas 40 is then sent back to the cavity 10 of the probe 1 and the cycle continues. It is therefore possible to measure the diffusivity of the soil gas 27.

Two measuring methods may be executed. The first method simply involves measuring and/or monitoring of soil gas concentration in the carrier gas 40, which is assumed to be in equilibrium with, and directly representative of, the soil gas environment directly outside the probe membrane.

The second method is more complex. Rates of soil gas diffusion are measured through a specific sequence of events, which can be broadly classified into four stages:
1) pre-measurement;
2) scrubbing;
3) re-equilibration; and
4) post-sequence measurement.

The pre-sequence stage is used to measure the initial soil gas concentration around the probe, which can be done using the probe 1, or by another separate method. Once the initial soil gas concentration is established, the concentration of this gas is removed from the carrier gas 40 either by "scrubbing" (flowing the gas across an absorbent chemical) or by purging with a gas mixture known to be free of the gas in question, or a particular component thereof. Upon the successful establishment of a zero (or near zero) concentration, the third stage is initiated. During this re-equilibration period, the natural soil gas 27 re-invades the carrier gas 40 by diffusive transport across the membrane 25. The rate at which this occurs is determined by the rate of diffusive gas transport in the soil, provided that the membrane 25 selected does not limit the rate of diffusion. Once the desired level of re-equilibration has been reached, the final stage of post-sequence concentration measurements are recorded by the system to establish the degree of re-equilibration that occurred during the allotted time interval. Calculations are performed by the test equipment 70 to determine the soil gaseous diffusion coefficient, based on the total mass flux of soil gas across the membrane surface area during the re-equilibration interval. For one-dimensional diffusional geometry, the solution for the diffusion coefficient is derived from the transient form of Fick's law.

In practical terms, the invention will be used to supplement information gathered in soil gas inquiries of many types. One example is as part of a monitoring program that documents the release of carbon dioxide from agricultural or forest soils, which is currently of major interest as a result of the magnitude of this source, its potential contribution to global warming, and potential management responses. Here, the invention can be fitted with a carbon dioxide sensor and used in its simplest form to measure the variations in concentration at a given depth within the soil by equilibration across the probe membrane. The second and more complex measurement method is also of use here because carbon dioxide release to the atmosphere is largely determined by the rate at which it can move upwards by diffusion. The invention can be used to quantify these rates of diffusive transport, which will help refine carbon dioxide emissions budgets at research sites.

The present invention has been described with regard to preferred embodiments. The description and the drawings were used to help the understanding, rather than to limit the scope, of the invention. It will be apparent to one skilled in the art that many modifications or variations may be brought to the invention without departing from the scope of the invention as described herein and are intended to be covered by the present description.

I claim:

1. A probe for sampling soil gas in situ comprising:
   a plastic body having a cavity and a waterproof membrane covering said cavity;
   said body also having an inlet communicating with said cavity for introducing a carrier gas, and an outlet communicating with said cavity for exhausting the carrier gas to a gas sensor;
   said waterproof membrane being permeable to the soil gas, such that when said probe is positioned in a soil gas measurement site, soil gas diffuses into said cavity and can combine with an introduced carrier gas and be exhausted therewith to the gas sensor.

2. A probe as defined in claim 1 wherein said body is elongate and said inlet and outlet are located at a first end thereof.

3. A probe as defined in claim 2 wherein said cavity has a longitudinal wall substantially separating said cavity into two chambers, said wall having an aperture for allowing fluid communication between said two chambers remote from said inlet and said outlet.

4. A probe as defined in claim 2 further comprising a gas sensor for measuring a concentration of a component of said soil gas.

5. A probe as defined in claim 2 further comprising a mesh around said membrane for protecting said membrane from being substantially deformed by the soil.

6. A probe as defined in claim 5 further comprising a first tube connected at one end to said inlet and at the other end to a carrier gas supply, and a second tube connected at one end to said outlet and at the other end to test equipment having a gas sensor for measuring a concentration of a component of the soil gas.

7. A probe as defined in claim 5 further comprising a pointed tip at a first end of said body for facilitating insertion of said probe in a soil by pushing on said probe.

8. A probe as defined in claim 7 wherein said inlet and said outlet are located at a second end of said body remote from said first end.

9. A probe as defined in claim 8, further comprising a peripheral enlargement of said body longitudinally located between said second end and said membrane.

10. A probe as defined in claim 9 further comprising a shaft connected at said second end for inserting said probe in said soil.

11. A probe as defined in claim 5 or claim 10 wherein said body is cylindrical.

12. A method for taking measurements of a soil gas in situ comprising the steps of:
    positioning a probe as recited in claim 1 below the surface of a soil site;
    operatively connecting said inlet and outlet to a gas sensor such as to form a closed-loop circuit;
    supplying a carrier gas at a substantially atmospheric pressure to said closed-loop circuit;
    circulating said carrier gas inside said closed-loop circuit.

13. A method as defined in claim 12 further comprising the step of taking measurements of a concentration of the soil gas diffused within said carrier gas.

14. A method for taking measurements of a soil gas in situ comprising circulating a carrier gas in a closed loop substantially at an atmospheric pressure both through a diffusion soil gas sampling probe positioned below the surface of a soil site and through a gas sensor, allowing a diffusion of a soil gas in the carrier gas, measuring an initial concentration of at least one component of the soil gas present in the carrier gas, changing said initial concentration of said at least one component of the soil gas present in the carrier gas after said initial concentration measuring, and deriving a diffusion coefficient from a transient form of Fick's law.

15. A method as defined in claim 14 wherein said probe is positioned below the surface of the soil site by being driven into the soil site by applying a downward force on a shaft connected to said probe.

16. A probe for sampling soil gas in situ comprising:
    a cylindrical body having a longitudinal cavity and a waterproof membrane covering said cavity;
    said body also having an inlet communicating with said cavity for introducing a carrier gas, and an outlet communicating with said cavity for exhausting the carrier gas to a gas sensor for measuring a concentration of a component of the soil gas, said inlet and said outlet being located at a first end of said body, said waterproof membrane being permeable to the soil gas, such that when said probe is positioned in a soil gas measurement site, soil gas diffuses into said cavity and can combine with an introduced carrier gas and be exhausted therewith to the gas sensor, said body further having a mesh around said membrane for protecting said membrane from being substantially deformed by the soil, said cavity having a longitudinal wall substantially separating said cavity into two chambers, said wall having an aperture for allowing fluid communication between said two chambers remote from said inlet and said outlet.

17. A probe as defined in claim 16 further comprising:
    a pointed tip at a second end of said body for facilitating insertion of said probe in the soil by pushing on said probe;
    a peripheral enlargement of said body longitudinally located between said second end and said membrane.

18. A probe as defined in claim 17 further comprising a shaft connected at said second end for driving said probe in said soil.

19. A method as defined in claim 14 further comprising allowing diffusion of said at least one component of the soil gas in the carrier gas after said changing, and subsequently measuring a second concentration of said at least one component of the soil gas in the carrier gas after an allotted time period of re-equilibration.

20. A soil gas measurement system comprising:
    a carrier gas;
    a gas sensor for measuring the concentration of at least one component of a soil gas in said carrier gas;
    a probe for sampling soil gas in situ having:
        a body having a cavity and a waterproof membrane covering said cavity;
        said body also having an inlet communicating with said cavity for introducing said carrier gas, and an outlet communicating with said cavity for exhausting said carrier gas to said gas sensor;
        said waterproof membrane being permeable to the soil gas, such that when said probe is positioned in a soil gas measurement site, soil gas diffuses into said cavity and can combine with said introduced carrier gas and be exhausted therewith to said gas sensor,
    a pump;
    a datalogger for logging data;
    a controller for controlling said gas sensor and said datalogger; and
    means to at least partially remove said at least one component of said soil gas from said carrier gas,
    wherein said gas sensor and said pump are fluidly connected to said probe through said inlet and said outlet, said pump circulating said carrier gas in a closed-loop circuit from said probe to said sensor and back to said probe, and said gas sensor operatively communicating with said datalogger.

21. measurement system as defined in claim 20 wherein said closed-loop circuit has low internal pressure gradients.

22. A system as defined in claim 20 wherein said sensor is located in said probe.

* * * * *